United States Patent
Ballard et al.

(10) Patent No.: US 9,615,859 B2
(45) Date of Patent: Apr. 11, 2017

(54) POSTED TRANSLATION SYSTEM AND METHOD

(71) Applicant: Warsaw Orthopedic, Inc., Warsaw, IN (US)

(72) Inventors: Rodney Ballard, Lakeland, TN (US); William Alan Rezach, Atoka, TN (US); Charles Dickinson, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 293 days.

(21) Appl. No.: 13/973,570

(22) Filed: Aug. 22, 2013

(65) Prior Publication Data
US 2015/0057708 A1 Feb. 26, 2015

(51) Int. Cl.
*A61B 17/88* (2006.01)
*A61B 17/70* (2006.01)

(52) U.S. Cl.
CPC ..... *A61B 17/7041* (2013.01); *Y10T 29/49963* (2015.01)

(58) Field of Classification Search
CPC ............ A61B 17/7037; A61B 17/7035; A61B 17/7041; A61B 17/7034; A61B 17/7049
USPC .................................................. 606/250–279
See application file for complete search history.

(56) References Cited

U.S. PATENT DOCUMENTS 7,678,112 B2 * 3/2010 Rezach ........................... 606/60
2010/0063546 A1 * 3/2010 Miller et al. ................... 606/278

* cited by examiner

*Primary Examiner* — Mary Hoffman
*Assistant Examiner* — Tara R Carter (57) ABSTRACT

Connector assemblies are provided to couple an elongate member extending along the spinal column to a bone engaging implant engaged to the spinal column. The connector assembly includes a coupler having an implant coupling portion and an elongate member coupling portion. The positioning and orientation of the coupler relative to the implant and elongate member can be adjusted to facilitate engagement of the connector assembly between the implant and elongate member.

18 Claims, 7 Drawing Sheets

POSTED TRANSLATION SYSTEM AND METHOD

TECHNICAL FIELD

The present disclosure generally relates to medical devices, systems and methods for the treatment of musculoskeletal disorders, and more particularly to a spinal implant fixation system that employs a connector for linear implants to provide stabilization of vertebrae.

BACKGROUND

Spinal implants can be engaged to or along one or more vertebrae of the spinal column for the treatment of various spinal conditions. Fasteners can be provided to secure the implant to a particular location along the spinal column. The implants can be provided to stabilize the spinal column for treatment, either by fixing the spinal column or by permitting at least some motion of the stabilized motion segments.

Multi-axial and uni-axial screws have been employed for securing elongated implants, such as rods or plates, along one or more motion segments of the spinal column. Such fasteners can comprise many components or parts that make placement and manipulation of the fastener and the elongated implant cumbersome during surgery to achieve the desired position relative to the spinal anatomy. Fasteners that facilitate securement of the elongated implant in a desired positioning along the spinal column can enhance spinal stabilization procedures.

SUMMARY

According to one aspect, a connector assembly includes a coupler for securing an elongate member to an implant engaged to the spinal column. The elongate member is offset to one side of and transversely oriented to the implant. The positioning and orientation of the elongate member and the implant can be adjusted relative to the coupler in a first configuration and locked in position in a second configuration.

According to another aspect, a system for stabilizing a bony segment, including an elongate member positionable along the bony segment; an implant engageable to the bony segment in a transverse orientation to the elongate member; and a connector assembly for connecting the elongate member to the implant, said connector assembly includes a coupler defining a receptacle for receiving the elongate member; a collar extending from the coupler, said collar defining an elongated slot for receiving a proximal portion of the implant therethrough in the transverse orientation relative to the elongate member; and an insert pivotably connected to said collar and within said receptacle.

According to another aspect, a connector for using in a system for stabilizing a bony segment, includes a coupler defining a receptacle for receiving an elongate member positionable along the bony segment; a collar extending from the coupler, said collar defining an elongated slot for receiving a proximal portion of an implant engageable to the bony segment in a transverse orientation to the elongate member; and an insert pivotably connected to said collar and within said receptacle.

According to another aspect, a method for coupling an elongate member to an implant engageable to a spinal column, includes providing a connector having a coupler defining a receptacle for receiving the elongate member therethrough and a collar secured to the coupler, the collar defining an elongated slot and extending transversely to the receptacle; positioning the elongate member through the receptacle of the coupler, the receptacle including an insert in contact with the elongate member pivotally received in the receptacle; positioning a proximal portion of the implant through the slot, the proximal portion of the implant including a sleeve positioned thereabout; advancing a setscrew through a bore in the coupler and into engagement with the elongate member; and clamping the sleeve to the proximal portion of the implant.

These and other aspects will be discussed further below.

BRIEF DESCRIPTION OF THE DRAWINGS

Like reference numerals indicate similar parts throughout the figures.

DETAILED DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

The exemplary embodiments of the system and method for measuring a surgical rod are discussed in terms of medical devices for the treatment of musculoskeletal disorders and more particularly, in terms of a spinal fixation system that provides stabilization for treating a vertebral column. It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is contemplated that the disclosed systems and methods may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of the posted translation system are fabricated from materials suitable for medical applications, including metals, polymers, ceramics, biocompatible materials and/or their composites, depending on the particular application and/or preference of a medical practitioner. For example, the elongated member, discussed below, of the spinal construct can be fabricated from materials such as titanium, thermoplastics such as polyaryletherketone (PAEK) including PEEK, PEKK and PEK, carbon-PEEK composites, PEEK-BaSO$_4$ polymeric rubbers, biocompatible materials such as polymers including plastics, metals, ceramics and composites thereof, rigid polymers including polyphenylene, polyamide, polyimide, polyetherimide, polyethylene, epoxy; and different sections of an elongated member, as discussed below, may have alternative material composites to achieve various desired characteristics such as strength, rigidity, elasticity, compliance biomechanical performance, durability and radiolucency or imaging preference.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. The following discussion includes a description of a connector assembly and methods in accordance with the principles of the present disclosure. Alternate embodiments are also disclosed. Reference will now be made in detail to the exemplary embodiments of the present disclosure, which are illustrated in the accompanying figures.

Figure 1:
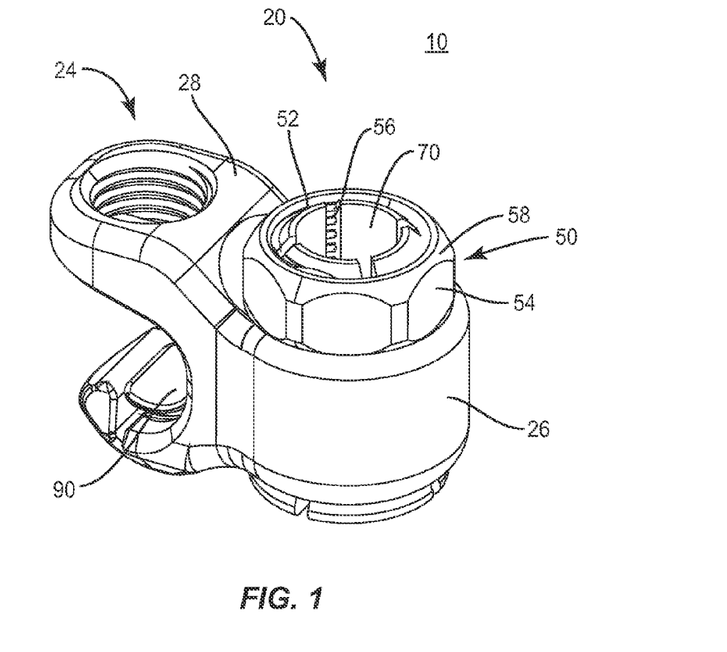
FIG. 1 is a perspective view of a connector assembly.
Figure 2:
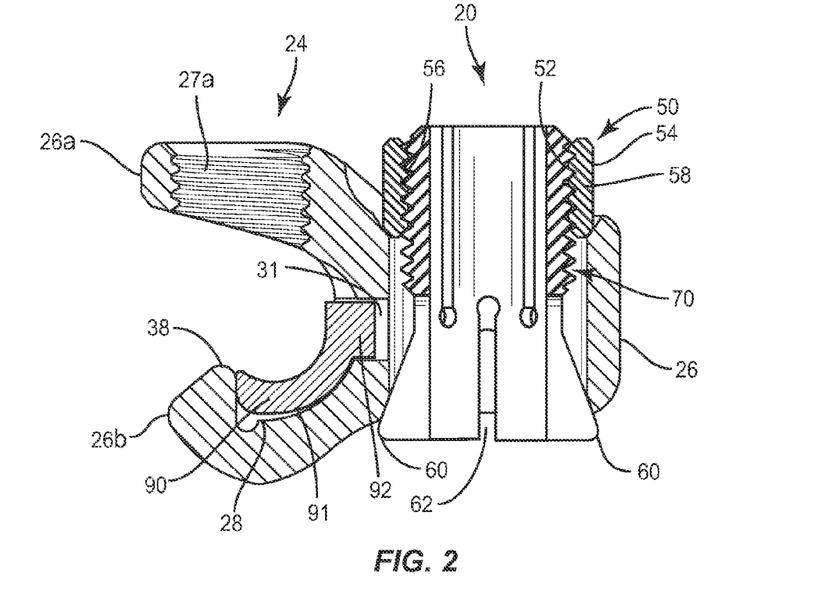
FIG. 2 is a section view of the connector assembly of FIG. 1.
Figure 3:
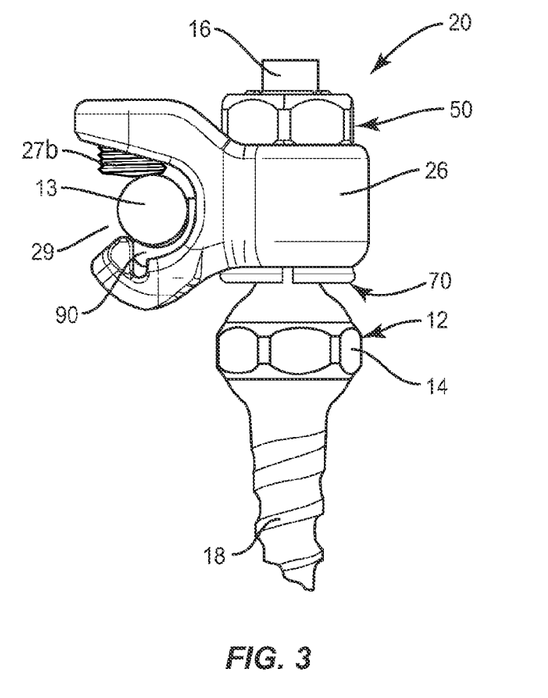
FIG. 3 is an elevation view of the connector assembly of FIG. 1 assembled with an anchor, shown in partial elevation view, and an elongate member, shown in section view.

FIGS. 1-3 show an embodiment of a connector assembly 10, and in FIG. 3 an implant 12 and elongate member 13 are shown coupled to connector assembly 10. Connector assembly 10 is operable to connect implant 12, such as a bone anchor, with elongate member 13, such as a spinal rod, to form an implant system. The distal end of implant 12 can be a bone screw or other suitable anchoring device engageable to bone or another implant. The implant can include a portion 16 for engagement with connector assembly 10. Elongate member 13 can be a spinal rod or other member positionable along the spinal column to maintain or assist in maintaining one or more vertebrae in a desired position.

Connector assembly 10 can include an implant coupling portion 20 extending through a coupler 24 of connector assembly 10. Implant coupling portion 20 can be engaged to a proximal portion 16 of implant 12. The proximal portion of implant 12 can also allow for connector assembly 10 to be positioned anywhere along the proximal portion 16, such as a reduction post or extended post implant. In one embodiment, proximal portion 16 can be a post, arm, or other suitable extension or portion for positioning through coupler 24. In a further embodiment, the implant coupling portion 20 can include an elongate body with a number of fingers or legs at each end that can clampingly engage the implant positioned in the elongate body.

Connector assembly 10 can also include a receptacle 29 in coupler 24 at a location offset to one side of implant 12. Elongate member 13 can extend through receptacle 29 and be engaged to coupler 24 in a transverse orientation to implant 12.

Implant 12 in the illustrated embodiment is a bone screw and can include a distal shaft 18 having a thread profile therealong for engaging bone, and an enlarged head 14 between distal shaft 18 and proximal portion 16. Head 14 can include flats or other tool engaging features therearound to engage a driving tool to facilitate engagement of implant 12 to the underlying bone. Various forms for implant 12 are contemplated, including threaded and non-threaded anchors, uni-planar and multi-axial pivoting arrangements. Bone engaging portions in the form of hooks, clamps, spikes, cables, interbody implants, fusion devices, non-cannulated screws, fenestrated screws, and bolts, are also contemplated, for example. In another form, the implant can be connected to another implant, and/or can be a bone plate, staple, and/or cross-connector extending between spinal rods, for example. In another form, the distal end of implant 12 can be a bone screw that transitions into a smooth post proximal portion 16 without including an enlarged head 14 located between the proximal and distal portions.

Elongate member 13 can be structured either alone or in combination with one or more other elongate members, implants and/or connector assemblies to provide a desired stabilization effect. In the illustrated embodiment, elongate member 13 is a spinal rod structured to extend between at least two connector assemblies 10 secured to the spinal column with corresponding bone engaging implants. Elongate member 13 can also extend between at least one connector assembly 10 and another implant having any type of suitable connection mechanism to secure elongate member 13 to the implant. Various forms for elongate member 13 are contemplated, including rods, tethers, cables, wires, and plates, for example.

Connector assembly 10 can include coupler 24 that includes a collar 26 having a slot 30 for receiving implant coupling portion 20 and implant 12 therethrough in a first direction. Coupler 24 can further include receptacle 29 for receiving elongate member 13 therethrough in a second direction that is transverse to the first direction. Furthermore, coupler 24 is arranged so that elongate member 13 is offset to one side of implant 12.

Receptacle 29 includes upper arm 26*a* and lower arm 26*b*. Lower arm 26*b* includes seat 28. Insert 90 is seated in seat 28 of lower arm 26*b*. Insert 90 includes saddle 91 and key 92. Key 92 is designed to mate with keyway 31 in collar 26. Once key 92 is inserted into keyway 31 and saddle 91 is seated within seat 28, insert 90 is retained within lower arm 26*b* by lip 38. When seated within lower arm 26*b*, insert 90 maintains an ability to swivel between first and second positions therein about an axis extending from the free end of key 92.

Upper arm 26*a* defines a bore 27 therein. Bore 27 includes a threaded inner surface 27*a*. Elongate member 13 rests upon saddle 91 of insert 90 when engaged within receptacle 29. Setscrew 27*b* is configured to threadingly engage with threaded inner surface 27*a* and pass through bore 27 to engage with elongate member 13. Setscrew 27*b* tightens to compress elongate member 13 onto insert 90 and affix elongate member 13 within receptacle 29.

Coupler 24 is shown in isolation in FIGS. 4-8. Coupler 24 includes collar 26 and receptacle 29. Collar 26 is connected to upper arm 26*a* and lower arm 26*b* that define receptacle 29. Lower arm 26*b* is configured to permit insert 90 to pivotably seat therein. Collar 26 includes a slot 30 extending therethrough transversely to receptacle 29. Slot 30 opens toward a respective one of the outer surfaces 34*a*, 34*b* along collar 26. Slot 30 includes a vertical wall surface 35 and sloped outer wall surfaces 36*a*, 36*b* that transitions from the vertical surface 35 to the outer surfaces 34*a*, 34*b*. Sloped surfaces 36*a*, 36*b* allow flare 60 (FIG. 11) and engaging member 50, respectively, to be recessed therein to provide a more low profile arrangement and to center flare 60 and engaging member 50 between the vertical walls surface 35 of slot 30.

Figure 4:
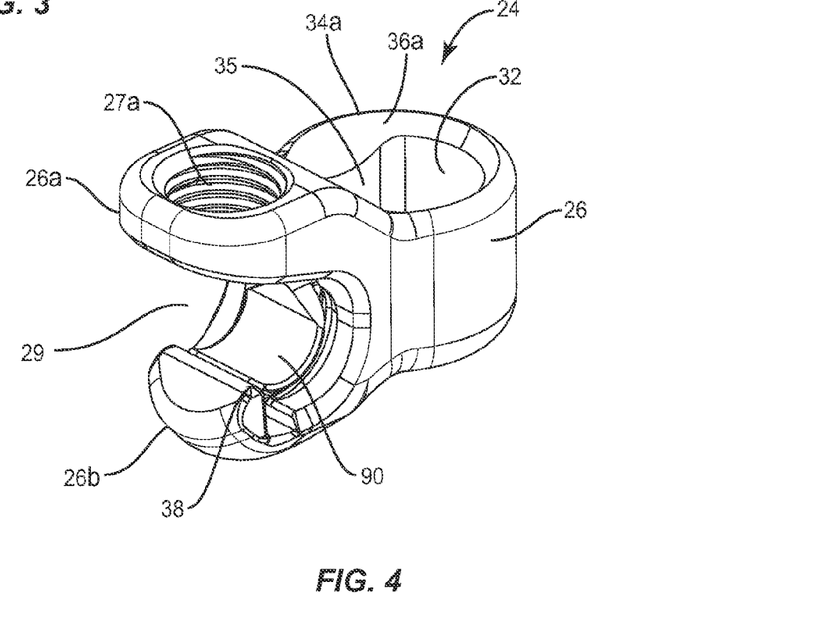
FIG. 4 is a perspective view of a coupler of the connector assembly of FIG. 1.
Figure 5:
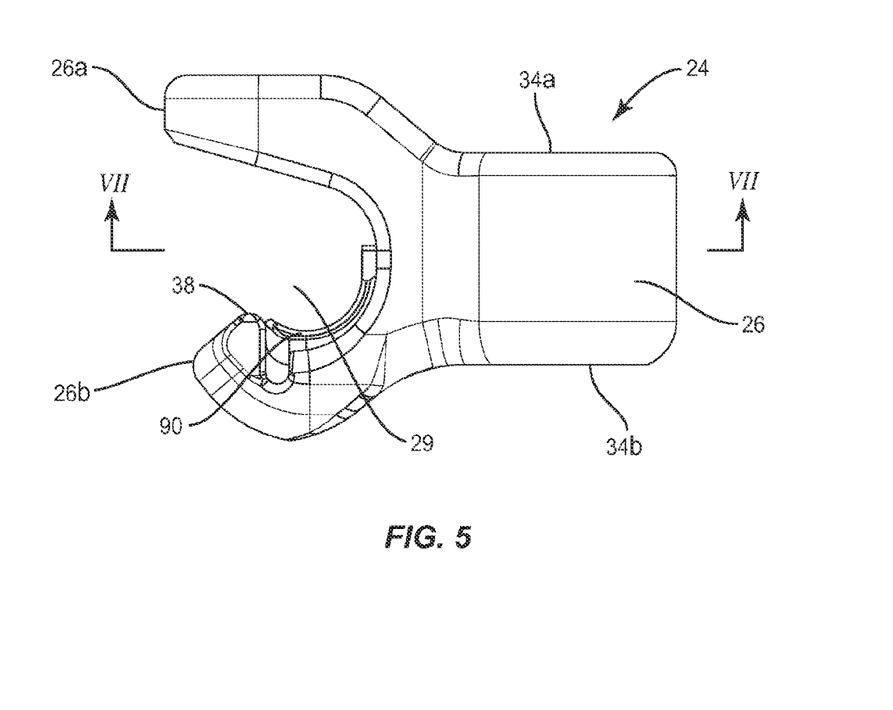
FIG. 5 is an elevation view of the coupler of FIG. 4.
Figure 6:
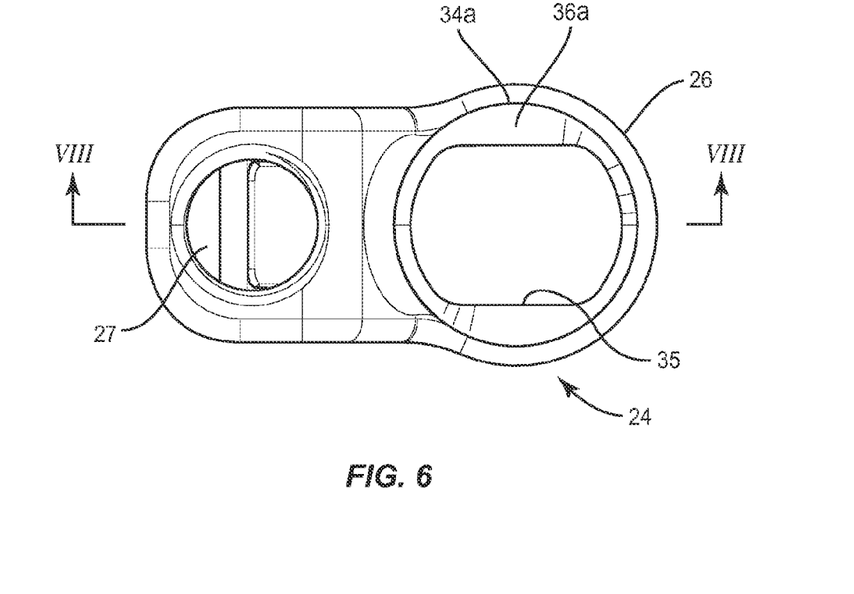
FIG. 6 is a plan view of the coupler of FIG. 4.
Figure 7:
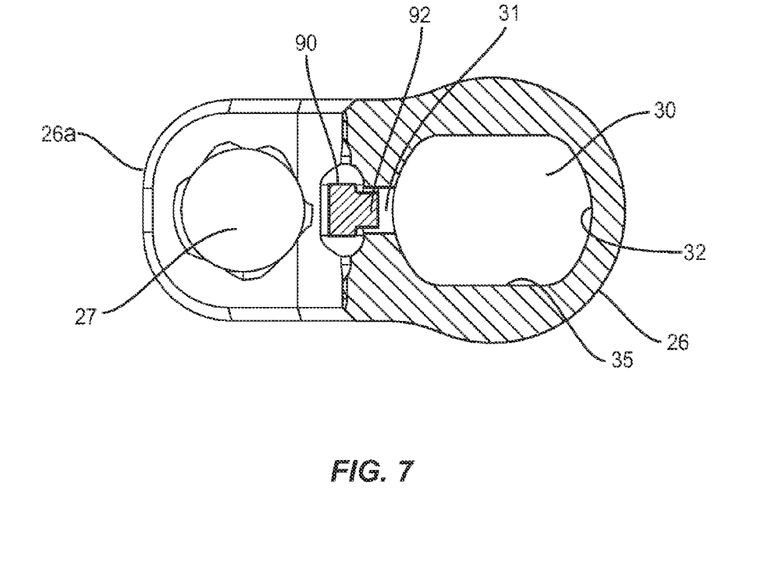
FIG. 7 is a section view through line 7-7 of FIG. 5.
Figure 8:
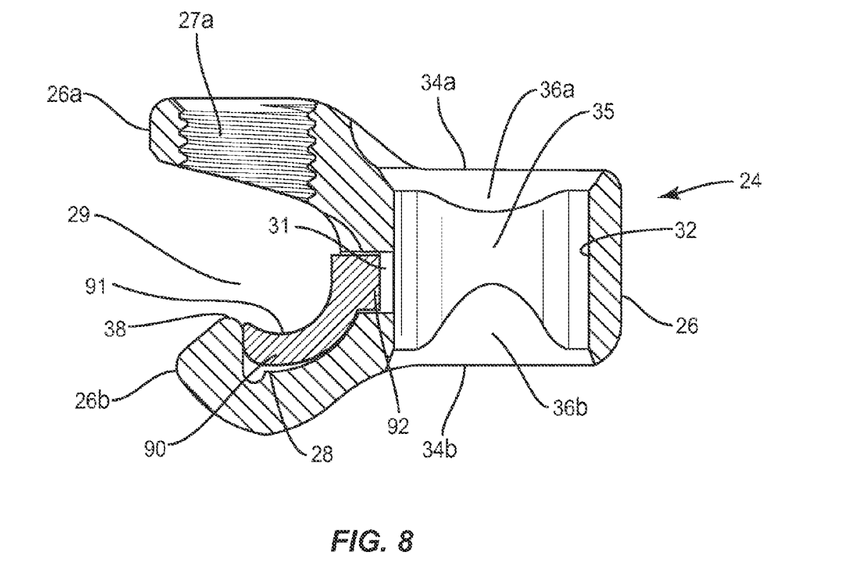
FIG. 8 is a section view through line 8-8 of FIG. 6.
Figure 9:
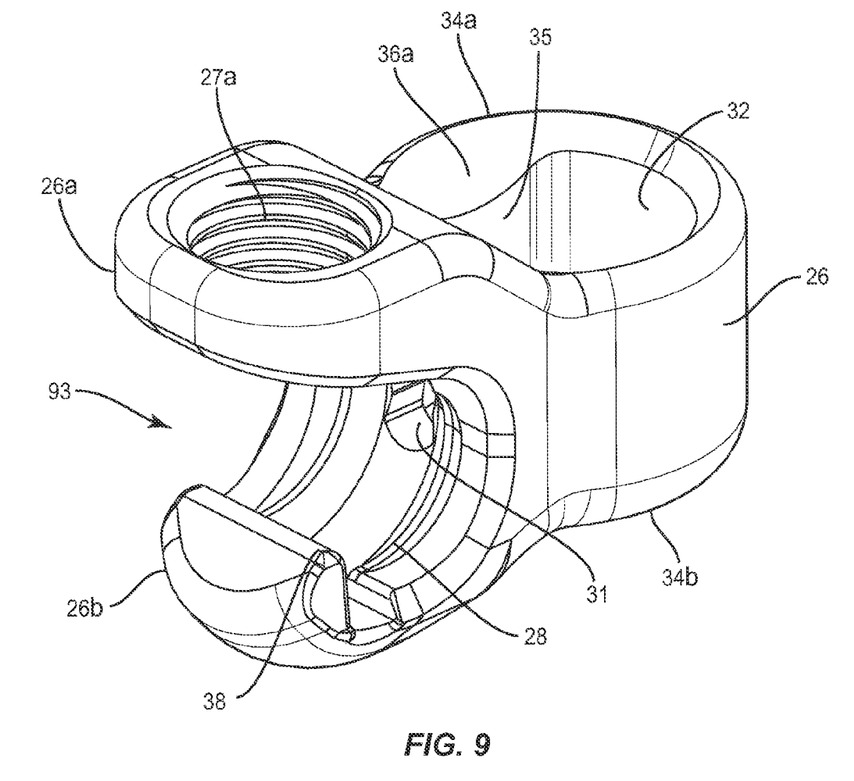
FIG. 9 is a perspective view of a coupler of the connector assembly of FIG. 1.

Sloped surfaces 36*a*, 36*b* and vertical wall surface 35 can provide a somewhat elongated arrangement in the medial-lateral direction and permit adjustability in the location of implant 12 relative to elongate member 13.

Implant coupling portion 20 includes a sleeve 70 positionable about proximal portion 16 of implant 12 and through slot 30. Implant coupling portion 20 also includes flare 60 positioned about and adjacent to the distal end of sleeve 70 for positioning in contact with sloped surface 36*b* of collar 26. Engaging member 50 is positionable about sleeve 70 and moveable therealong to contact sloped surface 36*a*. Engaging member 50 is movable along sleeve 70 to compress collar 26 of coupler 24 between engaging member 50 and flare 60, which in turn compresses sleeve 70 about proximal portion 16 of implant 12 to secure connecting assembly 10 thereto.

The arrangement of connector assembly 10 allows the positioning of coupler 24 relative to implant 12 to be adjusted as needed to accommodate the spinal anatomy while maintaining a low profile in the medial-lateral direction and a nearly tangential proximity of the implant 12 and elongate member 13. Medial-lateral adjustability can be provided by collar 26 of coupler 24 extending in the medial-lateral direction in the implantation orientation for a posterior surgical stabilization procedure. Furthermore, the orientation of the portion of the implant extending through slot 30 can be varied at various angles. For example, collar 26 can be obliquely angled to the longitudinal axis of the implant. Receptacle 29 provides rotational and angular adjustability of coupler 24 about elongate member 13 through the swivel movement of insert 90. Collar 26 can be obliquely angled relative to elongate member 13. Setscrew 27*b* engaging with elongate member 13 maintains the positioning of elongate member 13 when coupler 24 is secured to implant 12. Furthermore, sleeve 70 can be adjusted in positioning along proximal portion 16 of implant 12, and secured to implant 12 at any one of a number of positions therealong by the clamping action of sleeve 70 about proximal portion 16 as engaging member 50 and flare 60 are secured against collar 26.

In the illustrated embodiment, sleeve 70 includes an elongated, cylindrical body 74 having a proximal threaded portion 76 along at least a portion of a length thereof. Sleeve 70 is sized and shaped to fit within and move along slot 30. However, it should be appreciated the sleeve 70 can be shaped or configured differently in other embodiments. Sleeve 70 is shown in isolation in FIGS. 11 and 12. Threaded portion 76 includes one or more flat sections 88. In one embodiment, sleeve 70 includes two flat sections 88 positioned substantially diametrically opposite each other along the outside of sleeve 70. An aperture 72 extends axially through sleeve 70.

Figure 11:
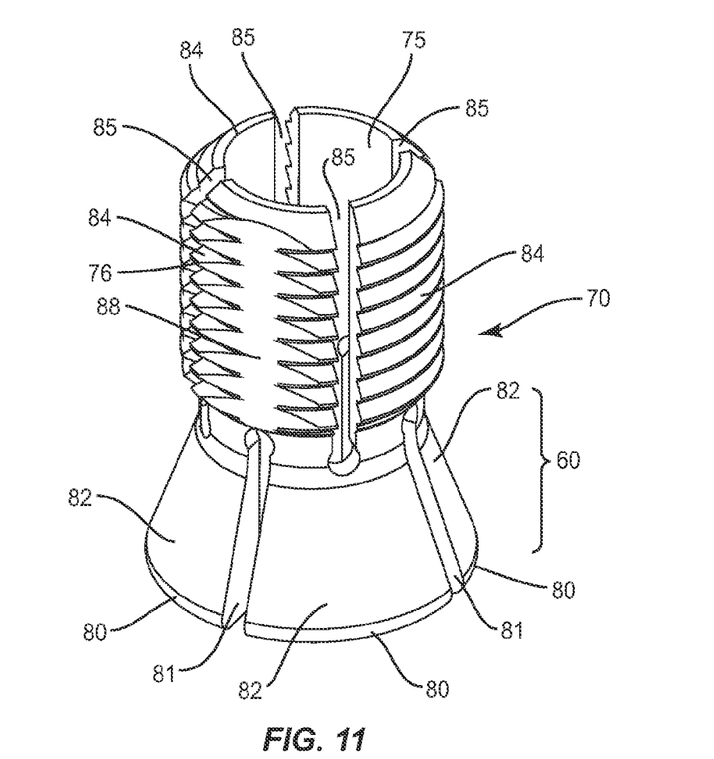
FIG. 11 is a perspective view of a sleeve of the connector assembly of FIG. 1.
Figure 12:
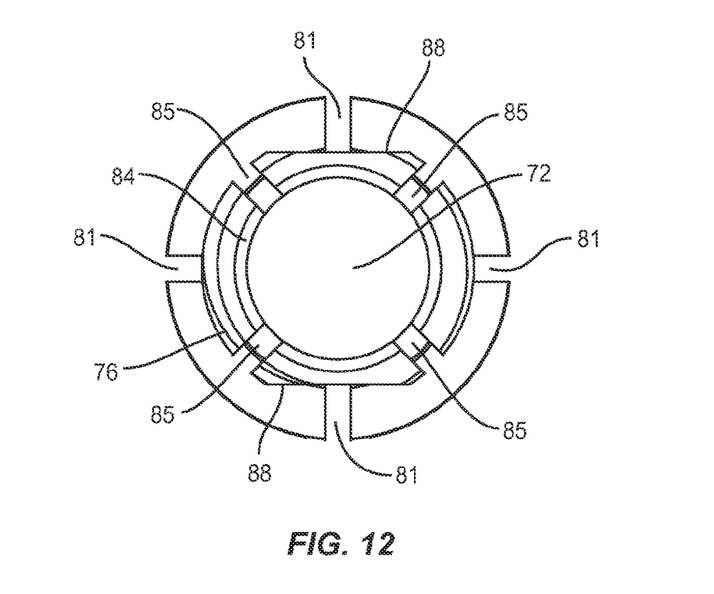
FIG. 12 is a top plan view of the sleeve of FIG. 11.

Proximal slots 85 extend through the wall of sleeve 70 along proximal portion 76 to form a plurality of proximal fingers 84. In the illustrated embodiment, there are four proximal slots 85 and four fingers 84 spaced equally about proximal portion 76. Other numbers of fingers and slots are also contemplated. Proximal fingers 84 can flex relative to one another to permit and facilitate clamping of proximal portion 76 of sleeve 70 about proximal portion 16 of implant 12 when engaging member 50 is secured thereto.

Sleeve 70 includes one or more axial slots 81 extending along a distal portion 78 thereof. Slots 81 also open distally in sleeve 70, forming a respective one of the legs 82 therebetween. In the illustrated embodiment, there are four slots 81 equally positioned about a circumference of sleeve 70 and which extend generally parallel to aperture 72. Other embodiments contemplate other numbers and spacing of slots and legs. Sleeve 70 further includes a foot 80 extending radially outwardly therefrom at the distal end of each of the legs 82. Feet 80 each include a proximally oriented convex surface adjacent a distal end of sleeve 70. The outer cross-sectional dimension of sleeve 70 at feet 80 is larger than an outer cross-sectional dimension of sleeve 70 at other locations along its length. The combination of feet 80 comprise flare 60.

Engaging member 50 includes a wall 58 extending about an internally threaded bore 52. Bore 52 includes internal threads 56 extending therearound, and engaging member 50 includes an outer surface 54 having flats or other suitable tool engaging structure that can be engaged by a tool to facilitate threadingly advancing engaging member 50 along sleeve 70. Engaging member 50 can compress the proximal fingers 84 of sleeve 70 toward aperture 72 to clamp implant 12 therein.

Coupler 24 and insert 90 are shown in isolation in FIGS. 9, 10, 13 and 14. Receptacle 29 includes a passage 93 extending therethrough to receive elongate member 13. Collar 26 includes keyway 31 positioned perpendicular to a longitudinal axis of collar 26 and facing passage 93. Keyway 31 has an hourglass shape and is designed to mate with key 92; other shapes of keyway 31 are contemplated. Key 92 is positioned on insert 90 and has a rectangular shape; other shapes of key 92 are contemplated. The rectangular shape of key 92 when mated with the hourglass shape of keyway 31 permits insert 90 to rock or swivel between a first and a second position as key 92 is moved from contact with surfaces 31a to surfaces 31b of keyway 31.

Figure 10:
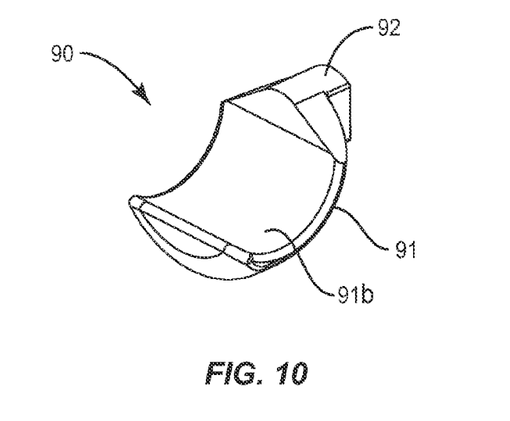
FIG. 10 is a perspective view of the insert of FIG. 1.
Figure 13:
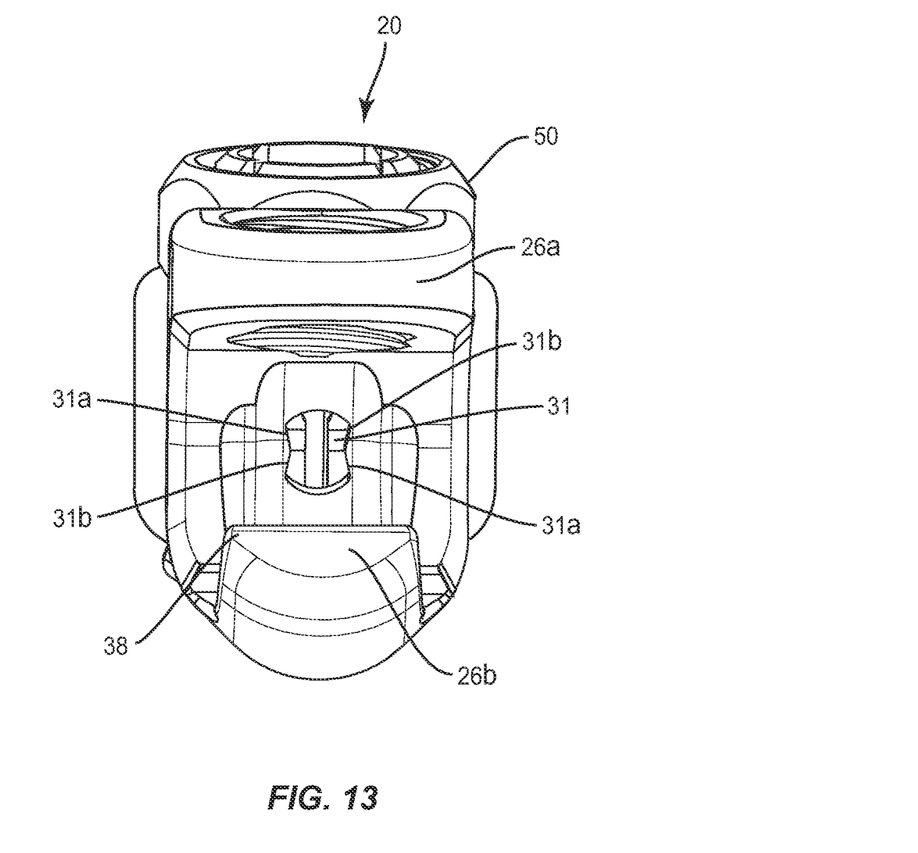
FIG. 13 is a front view of the coupler of FIG. 4.
Figure 14:
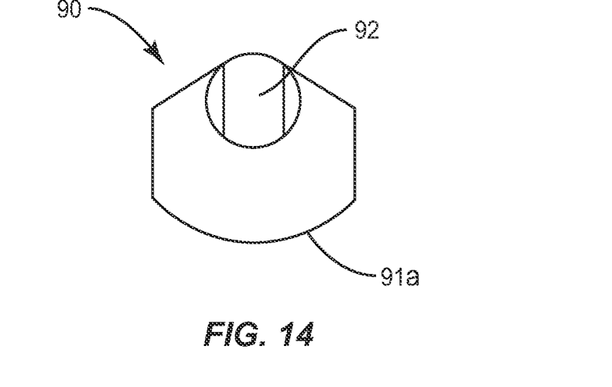
FIG. 14 is a rear view of the insert of FIG. 4.

Included on lower arm 26b is seat 28 having an arcuate shape and sloping surface between keyway 31 and lip 38. Insert 90 includes a saddle 91 having a lower surface 91a. An upper surface 91b of saddle 90 is designed to closely mate with elongate member 13. The upper surface 91b can have differing dimensions to mate with elongate members of differing diameters. Lower surface 91a is also arcuate in design and shaped to complement the sloping surface between keyway 31 and lip 38. The arcuate and sloping surface design permit free movement of insert 90 between the first and second positions.

In use, connector assembly 10 can be used in surgical procedures relating to the spine. The surgeon can gain access to a surgical site using any suitable technique, such as through an incision and retraction of tissue, or through minimally invasive access portals or pathways. One or more of the implants 12 can be provided in the form of bone screws can be threadingly implanted into one or more vertebrae, such as in the pedicle in a posterior stabilization procedure. Proximal portion 16 can extend from the pedicle. If not pre-positioned on proximal portion 16, sleeve 70 can be positioned on implant 12.

Insert 90 can be positioned within receptacle 29 with insert 90 loosely retained in receptacle 29. Elongate member 13 can be positioned into receptacle 29 and seated upon saddle 91. Setscrew 27b can be positioned in bore 27. It is contemplated that assembly of coupler 24 with elongate member 13 can be completed prior to implantation of elongate member 13 or during implantation. In either case, elongate member 13 can be positioned along the spinal column with coupler 24 secured thereto and collar 26 extending medial-laterally from elongate member 13. Coupler 24 can then be positioned over implant 12 with proximal portion 16 and sleeve 70 extending through slot 30. Prior to finally securing coupler 24, the orientation of elongate member 13 relative to coupler 24 can be adjusted by pivoting insert 90 in receptacle 29. In addition, the positioning of implant 12 in collar 26 can be adjusted by moving coupler 24 along the implant in slot 30.

Engaging member 50 is positioned about sleeve 70 and threaded distally therealong to contact collar 26. Further advancement of engaging member 50 along sleeve 70 seats collar 26 against flare 60 to push distally on feet 80. Flare 60 causes sleeve 70 to flex inwardly about legs 82, and into clamping engagement with proximal portion 16 of implant 12.

In spinal surgical procedures, elongate member 13 and one or more connector assemblies 10 and other implants discussed herein may be employed unilaterally. Alternatively, a second elongate member 13 and one or more connector assemblies 10 and/or other suitable connection mechanism with other implants can be secured to the other side of the vertebral level or levels to be stabilized. Multiple elongate members 13 and corresponding implant/connector assemblies 10 can be secured along the same side of the spinal column in either uni-lateral or bi-lateral stabilization procedures.

In one technique, the underlying bone forms a portion of a vertebral body of the spinal column. The underlying bone can be a part of the anterior, oblique, antero-lateral, lateral or posterior vertebral elements, including the pedicle, spinous process, transverse processes, lamina or facet, for example. Applications in techniques along any portion or portions of the spinal column are contemplated, including the cervical, thoracic, lumbar and sacral regions. The connector assemblies, implants and elongate members can be positioned along the spinal column in invasive procedures where skin and tissue are dissected and retracted to expose the implant locations, or in minimally invasive procedures where one or more of the connector assemblies, elongate members and/or implants are guided through at least the tissue or access portals adjacent the column to the desired implantation location Engaging member 50 is engageable about sleeve 70 to secure implant 12 in engagement with coupler 24. Coupler 24 can be at any position along implant 12. Engaging member 50 can include a proximal break-off portion (not shown) that severs upon application of a threshold torque, although embodiments without a break-off portion are contemplated as shown. Sleeve 70 is illustrated as an externally threaded sleeve that engages the internal thread profile along engaging member 50. Other configurations are also contemplated for engagement with engaging member 50 and flare 60, including multiple component members including internally and/or externally threaded portions, frictional engagement, shape memory materials, snap fits, clamps and bayonet-locks, for example. Coupler 24 can then be attached to elongate member 13 via a translation method. In another technique, coupler 24 can first be attached to elongate member 13 and then be positioned along implant 12.

Another embodiment is considered that does not include saddle 90. In this embodiment, the elongate member would contact lower arm 26b. In this embodiment the elongate member would be positioned at an angle approximately perpendicular to implant 12.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for stabilizing a bony segment, comprising:
   an elongate member positionable along the bony segment;
   an implant engageable to the bony segment in a transverse orientation to the elongate member; and
   a connector assembly for connecting the elongate member to the implant, said connector assembly comprising:
      a coupler defining a receptacle for receiving the elongate member;
      a collar extending from the coupler, said collar defining an elongated slot for receiving a proximal portion of the implant therethrough in the transverse orientation relative to the elongate member; and
      an insert pivotably connected to said collar and within said receptacle, said insert including a key extending perpendicular to said elongate member and into a keyway defined in said collar such that the insert swivels between first and second positions about an axis defined by a free end of the key;
      wherein said key has a rectangular configuration configured to mate with an hourglass configuration of said keyway such that said insert can rotate swivel between the first position and the second position.

2. The system of claim 1, wherein a distance between said elongate member and said implant can be varied by varying a position of said proximal portion of said implant in said slot.

3. The system of claim 1, wherein said insert includes a saddle having an arcuate configuration for receiving said elongate member.

4. The system of claim 1, wherein said connector assembly further comprises:
   an implant coupling portion positioned about said proximal portion of said implant, said implant coupling portion comprising:
   a sleeve having an axially extending aperture for receiving said proximal portion and having outwardly extending portions adjacent a distal end thereof; and
   an engaging member engageable about said sleeve along a proximal end of said sleeve,
   wherein said collar is positioned between said outwardly extending portions and said engaging member, and
   wherein said outwardly extending portions are movable from an opened configuration to a closed configuration as said engaging member is threadingly advanced along said sleeve toward said collar.

5. The system of claim 4, wherein said sleeve includes a number of proximal slots extending axially along a portion of a length thereof from a proximal end of said sleeve, said proximal slots dividing said sleeve into a number of proximal fingers moveable toward one another to grip said proximal portion of said implant therebetween.

6. The system of claim 5, wherein said sleeve includes a number of distal slots extending axially along a portion of a length therefrom from a distal end of said sleeve, said distal slots dividing said sleeve into a number of distal legs, said outwardly extending portions forming a flare adjacent a distal end of said legs, said legs being moveable toward one another to grip said proximal portion of said implant therebetween.

7. The system of claim 6, wherein said engaging member is movable along said sleeve into contact with said collar and compress said collar between said engaging member and said flare, and moving said legs toward one another to grip said proximal portion of said implant as said engaging member and said flare are tightened against said collar.

8. The system of claim 1, wherein said collar comprises an inner surface comprising a lip that extends perpendicular to the elongate member and an arcuate seat extending from the lip, the insert comprising a saddle that is seated within the seat.

9. The system of claim 8, wherein:
   said coupler comprises spaced apart arms upper and lower that define the receptacle therebetween, the lower arm comprising the lip and the seat;
   said insert is retained within lower arm by said lip.

10. The system of claim 1, wherein said coupler comprises a passage that is in communication with the receptacle and opens away from the implant.

11. The system of claim 1, wherein said implant comprises a distal portion comprising a bone screw, a proximal portion comprising a post that extends parallel to the bone screw and a head positioned between the distal portion and the proximal portion.

12. The system of claim 11, wherein said proximal portion is positioned in said elongated slot and said head has a maximum diameter that is greater than that of said elongated slot.

13. A connector for using in a system for stabilizing a bony segment, comprising:
   a coupler defining a receptacle for receiving an elongate member positionable along the bony segment;
   a collar extending from the coupler, said collar defining an elongated slot for receiving a proximal portion of an implant engageable to the bony segment in a transverse orientation to the elongate member; and
   an insert pivotably connected to said collar and within said receptacle, said insert including a key extending perpendicular to said elongated slot and into a keyway defined in said collar such that the insert swivels between first and second positions about an axis defined by a free end of the key;
   wherein said key has a rectangular configuration configured to mate with an hourglass configuration of said keyway such that said insert can rotate swivel between the first position and the second position as said key moves within said keyway.

14. The connector of claim 13, wherein said insert includes a saddle having an arcuate configuration for receiving said elongate member.

15. The connector of claim 13, wherein said connector assembly further comprises:
   an implant coupling portion positioned about said proximal portion of said implant, said implant coupling portion comprising:
      a sleeve having an axially extending aperture for receiving said proximal portion and having outwardly extending portions adjacent a distal end thereof; and
      an engaging member engageable about said sleeve along a proximal end of said sleeve,
   wherein said collar is positioned between said outwardly extending portions and said engaging member, and
   wherein said outwardly extending portions are movable from an opened configuration to a closed configuration as said engaging member is threadingly advanced along said sleeve toward said collar.

16. The connector of claim 13, wherein said implant is a bone screw with a threaded shaft distal of said proximal portion.

17. The connector of claim 13, wherein a distance between said elongate member and said implant can be varied by varying a position of said proximal portion of said implant in said slots.

18. A connector for using in a system for stabilizing a bony segment, comprising:
- a coupler defining a receptacle for receiving an elongate member positionable along the bony segment;
- a collar extending from the coupler, said collar defining an elongated slot for receiving a proximal portion of an implant engageable to the bony segment in a transverse orientation to the elongate member; and
- an insert pivotably connected to said collar and within said receptacle,
- wherein said insert includes a key extending perpendicular to said elongate member and into a keyway defined in said collar, and
- wherein said key has a rectangular configuration configured to mate with an hourglass configuration of said keyway such that said insert can rotate between a first position and a second position as said key moves within said keyway.

\* \* \* \* \*

UNITED STATES PATENT AND TRADEMARK OFFICE
CERTIFICATE OF CORRECTION

PATENT NO. : 9,615,859 B2  
APPLICATION NO. : 13/973570  
DATED : April 11, 2017  
INVENTOR(S) : Ballard et al.

Page 1 of 1

It is certified that error appears in the above-identified patent and that said Letters Patent is hereby corrected as shown below:

In the Specification

Column 4, Line 8, delete "epoxy;" and insert -- epoxy, --, therefor.

Column 7, Line 38, delete "saddle 90" and insert -- saddle 91 --, therefor.

Column 8, Line 59, delete "saddle 90." and insert -- saddle 91. --, therefor.

Signed and Sealed this  
Twentieth Day of March, 2018

Andrei Iancu  
*Director of the United States Patent and Trademark Office*